United States Patent
Post

(10) Patent No.: US 10,327,849 B2
(45) Date of Patent: Jun. 25, 2019

(54) ROBOTIC SYSTEM AND METHOD FOR BACKDRIVING THE SAME

(71) Applicant: MAKO Surgical Corp., Ft. Lauderdale, FL (US)

(72) Inventor: Nicholas Jon Post, Kalamazoo, MI (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 158 days.

(21) Appl. No.: 15/342,587

(22) Filed: Nov. 3, 2016

(65) Prior Publication Data
US 2017/0128136 A1 May 11, 2017

Related U.S. Application Data

(60) Provisional application No. 62/253,994, filed on Nov. 11, 2015, provisional application No. 62/255,610, filed on Nov. 16, 2015.

(51) Int. Cl.
*A61B 34/10* (2016.01)
*A61B 34/30* (2016.01)
(Continued)

(52) U.S. Cl.
CPC .............. *A61B 34/10* (2016.02); *A61B 34/30* (2016.02); *A61B 34/76* (2016.02); *B25J 9/1633* (2013.01);
(Continued)

(58) Field of Classification Search
CPC ......... A61B 34/10; A61B 34/30; A61B 34/76; A61B 2034/102; A61B 50/13;
(Continued)

(56) References Cited

U.S. PATENT DOCUMENTS

| 6,046,727 A | 4/2000 | Rosenberg et al. |
|---|---|---|
| 6,246,200 B1 | 6/2001 | Blumenkranz et al. |

(Continued)

FOREIGN PATENT DOCUMENTS

| EP | 2332478 A2 | 6/2011 |
|---|---|---|
| EP | 2332479 A2 | 6/2011 |

(Continued)

OTHER PUBLICATIONS

International Search Report of PCT/US2016/060269; dated Feb. 28, 2017 12 pages.

*Primary Examiner* — Bao Long T Nguyen
(74) *Attorney, Agent, or Firm* — Howard & Howard Attorneys PLLC

(57) ABSTRACT

A robotic surgical systems and methods of operating the same are provided. The system comprises a surgical tool, a manipulator having a plurality of joints and supporting the surgical tool, and a controller. A virtual simulation represents the surgical tool as a virtual rigid body having a virtual mass including an inertia about at least one of the joints. The controller determines an expected joint torque for the joint. The expected joint torque is compared to an actual joint torque of the joint to determine a joint torque difference. The inertia of the virtual mass about the joint is determined. An angular acceleration about the joint is computed using the joint torque difference and the inertia. The angular acceleration is projected to the virtual mass to determine an external force. The controller simulates dynamics of the surgical tool in the virtual simulation in response to the external force.

21 Claims, 10 Drawing Sheets

(51) Int. Cl.
  *A61B 34/00* (2016.01)
  *B25J 9/16* (2006.01)
  *B25J 13/08* (2006.01)
  *A61B 50/13* (2016.01)

(52) U.S. Cl.
  CPC ............ *B25J 13/085* (2013.01); *A61B 50/13* (2016.02); *A61B 2034/102* (2016.02)

(58) Field of Classification Search
  CPC ..... A61B 34/101; B25J 9/1633; B25J 13/085; G05B 2219/40318
  USPC ................................ 700/245, 250, 260, 261
  See application file for complete search history.

(56) References Cited

U.S. PATENT DOCUMENTS

| | | | |
|---|---|---|---|
| 6,441,577 B2 | 8/2002 | Blumenkranz et al. | |
| 6,451,027 B1 | 9/2002 | Cooper et al. | |
| 6,459,926 B1 | 10/2002 | Nowlin et al. | |
| 6,659,939 B2 | 12/2003 | Moll et al. | |
| 7,087,049 B2 | 8/2006 | Nowlin et al. | |
| 7,212,886 B2 | 5/2007 | Nagata et al. | |
| 7,390,325 B2 | 6/2008 | Wang et al. | |
| 7,623,944 B2 | 11/2009 | Dariush | |
| 7,646,161 B2 | 1/2010 | Albu-Schaffer et al. | |
| 7,806,891 B2 | 10/2010 | Nowlin et al. | |
| 7,843,158 B2 | 11/2010 | Prisco | |
| 8,004,229 B2 | 8/2011 | Nowlin et al. | |
| 8,140,189 B2 | 3/2012 | Nagasaka | |
| 8,155,790 B2 | 4/2012 | Oga et al. | |
| 8,405,340 B2 | 3/2013 | Moon et al. | |
| 8,428,779 B2 | 4/2013 | Ohga et al. | |
| 8,489,238 B2 | 7/2013 | Ooga et al. | |
| 8,541,970 B2 | 9/2013 | Nowlin et al. | |
| 8,624,537 B2 | 1/2014 | Nowlin et al. | |
| 8,644,988 B2 | 2/2014 | Prisco et al. | |
| 8,650,965 B2 | 2/2014 | Hashiguchi et al. | |
| 8,740,882 B2 | 6/2014 | Jun et al. | |
| 8,749,189 B2 | 6/2014 | Nowlin et al. | |
| 8,749,190 B2 | 6/2014 | Nowlin et al. | |
| 8,770,905 B2 | 7/2014 | Al-Mouhamed et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 8,843,236 B2 | 9/2014 | Barajas et al. | |
| 8,965,576 B2 | 2/2015 | Chen et al. | |
| 9,060,796 B2 | 6/2015 | Seo | |
| 9,259,281 B2 | 2/2016 | Griffiths et al. | |
| 9,820,818 B2 * | 11/2017 | Malackowski | ........ A61B 34/30 |
| 2003/0013949 A1 | 1/2003 | Moll et al. | |
| 2007/0013336 A1 | 1/2007 | Nowlin et al. | |
| 2007/0151389 A1 * | 7/2007 | Prisco | .................... B25J 9/1633 74/490.05 |
| 2009/0248038 A1 | 10/2009 | Blumenkranz et al. | |
| 2010/0312392 A1 | 12/2010 | Zimmermann | |
| 2011/0082587 A1 | 4/2011 | Ziaei et al. | |
| 2011/0190932 A1 | 8/2011 | Tsusaka et al. | |
| 2011/0264108 A1 | 10/2011 | Nowlin et al. | |
| 2011/0264109 A1 | 10/2011 | Nowlin et al. | |
| 2011/0264110 A1 | 10/2011 | Nowlin et al. | |
| 2011/0270271 A1 | 11/2011 | Nowlin et al. | |
| 2012/0283747 A1 | 11/2012 | Popovic | |
| 2013/0116706 A1 | 5/2013 | Lee et al. | |
| 2013/0178868 A1 | 7/2013 | Roh | |
| 2014/0039617 A1 | 2/2014 | Bowling et al. | |
| 2014/0039681 A1 | 2/2014 | Bowling et al. | |
| 2014/0052153 A1 | 2/2014 | Griffiths et al. | |
| 2014/0052154 A1 | 2/2014 | Griffiths et al. | |
| 2014/0081461 A1 | 3/2014 | Williamson et al. | |
| 2014/0121837 A1 | 5/2014 | Hashiguchi et al. | |
| 2014/0222207 A1 | 8/2014 | Bowling et al. | |
| 2014/0276952 A1 | 9/2014 | Hourtash et al. | |
| 2014/0276953 A1 | 9/2014 | Swarup et al. | |
| 2014/0276954 A1 | 9/2014 | Hourtash | |
| 2014/0277742 A1 | 9/2014 | Wells et al. | |
| 2014/0379126 A1 | 12/2014 | Ueberle | |
| 2015/0032126 A1 | 1/2015 | Nowlin et al. | |
| 2015/0051733 A1 | 2/2015 | Nowlin et al. | |
| 2015/0081098 A1 | 3/2015 | Kogan | |
| 2015/0127151 A1 | 5/2015 | Riedel et al. | |

FOREIGN PATENT DOCUMENTS

| | | |
|---|---|---|
| EP | 2332480 A2 | 6/2011 |
| EP | 2332482 A2 | 6/2011 |
| EP | 1885273 B1 | 2/2012 |
| EP | 2332483 B1 | 4/2017 |
| WO | 2006124390 A2 | 11/2006 |
| WO | 2010088959 A1 | 8/2010 |
| WO | 2011109041 A1 | 9/2011 |
| WO | 2014151550 A2 | 9/2014 |
| WO | 2015127078 A1 | 8/2015 |

* cited by examiner

ROBOTIC SYSTEM AND METHOD FOR BACKDRIVING THE SAME

CROSS-REFERENCE TO RELATED APPLICATIONS

The subject application claims the benefit of U.S. Provisional Patent Application No. 62/253,994, filed Nov. 11, 2015, and U.S. Provisional Patent Application No. 62/255,610, filed Nov. 16, 2015, the contents of each being hereby incorporated by reference in their entirety.

TECHNICAL FIELD

The present invention relates generally to a robotic system and a method for backdriving employed by the robotic system.

BACKGROUND

Force control in robotics is conventionally implemented using either impedance control or admittance control. One example of an impedance control feedback loop is illustrated in FIG. 1. With impedance control, positions of the joints of the robot are inputted into the controller and joint torques for controlling movement of the robot are outputted and applied. In other words, the impedance controller determines position and applies (or commands) force/torque. In FIG. 1, the impedance controller applies specific joint torques to the joints. If the robot experiences external force acting on one of the joints, for example, the impedance control system does not calculate or measure such force. Instead, the impedance controller merely re-determines the robot position and re-calculates the requisite force to be applied.

Conventional impedance control may provide stable control when contacting rigid environments and may provide a light feel when engaging soft environments. However, impedance control can give the robot an unstable loose feel and may introduce errors when interacting with stiff virtual constraints, such as haptic boundaries, which limit movement of the robot.

Admittance control, on the other hand, is the inverse of impedance control. One example of an admittance control feedback loop is illustrated in FIG. 2. With admittance control, rather than determining position and commanding force, the controller instead determines applied force/torque and commands position. A force-torque sensor or joint torque measurements are used to detect input force to the system. Based on the detected input force, and knowing a current position of the joints based on measured joint angles, the admittance controller commands a new position of the joints by applying determined joint torques to move the joints accordingly.

Conventional admittance control can give the robot stable rigid feel and may reduce errors when interacting with virtual constraints, such as haptic boundaries. However, a robot subject to admittance control may feel heavy to a user and may overreact when contacting rigid environments. As significantly, using a single admittance controller that utilizes either the force/torque sensor or the joint torques to measure external force(s) acting on one or more of the joints provides significant challenges. Mainly, when the robot experiences such external forces, the location(s) (e.g., the joint(s)) to which the external forces are applied are unknown thereby potentially resulting in undesired dynamic behavior of the robot.

SUMMARY

One embodiment of a robotic surgical system is provided. The robotic surgical system includes a surgical tool and a manipulator supporting the surgical tool. The manipulator comprises a plurality of joints and a plurality of joint actuators. A controller is in communication with the manipulator and is configured to simulate dynamics of the surgical tool in a virtual simulation by representing the surgical tool as a virtual rigid body having a virtual mass. The virtual mass has an inertia about at least one of the joints. The controller is configured to determine an expected joint torque for the at least one joint. The controller compares the expected joint torque to an actual joint torque of the at least one joint to determine a joint torque difference. The inertia of the virtual mass about the at least one joint is determined. The controller computes an angular acceleration about the at least one joint using the joint torque difference and the inertia. The angular acceleration is projected to the virtual mass to determine an external force. The controller simulates dynamics of the surgical tool in the virtual simulation in response to the external force. Action of the joint actuators is commanded in accordance with the virtual simulation.

One embodiment of a method of operating a robotic surgical system is provided. The robotic surgical system comprises a surgical tool, a manipulator supporting the surgical tool and comprising a plurality of joints, a plurality of actuators, and a controller being in communication with the manipulator. A virtual simulation represents the surgical tool as a virtual rigid body having a virtual mass. The virtual mass has an inertia about at least one of the joints. The method includes determining with the controller an expected joint torque for the at least one joint. The controller compares the expected joint torque to an actual joint torque of the at least one joint to determine a joint torque difference. The inertia of the virtual mass about the at least one joint is determined. The controller computes an angular acceleration about the at least one joint using the joint torque difference and the inertia. The angular acceleration is projected to the virtual mass to determine an external force. The controller simulates dynamics of the surgical tool in the virtual simulation in response to the external force. Action of the joint actuators is commanded in accordance with the virtual simulation.

One embodiment of a method of backdriving a robotic system is provided. The robotic system includes a tool, a manipulator supporting the tool and including a plurality of joints, a plurality of actuators, and a controller being in communication with the manipulator. A virtual simulation represents the tool as a virtual rigid body having a virtual mass. The virtual mass has an inertia about each of the joints. The method comprises determining with the controller an expected joint torque for each joint individually. The controller compares the expected joint torque to an actual joint torque to determine a joint torque difference for each joint individually. The controller determines the inertia of the virtual mass about each joint individually. An angular acceleration about each joint individually is computed using the joint torque difference and the inertia. An acceleration of the virtual mass is obtained in more than one degree of freedom using the angular accelerations of the plurality of joints in combination. The controller projects the angular acceleration to the virtual mass in more than one degree-of-freedom to determine an external force. The controller simulates dynamics of the tool in the virtual simulation in response to the external force. Action of the joint actuators is commanded in accordance with the virtual simulation.

The system and method solve at least the aforementioned problems by determining the external force, which is compatible with the controller. That is, the system and method resolve issues with single admittance controllers. Mainly, when the robot experiences such external force, the location (e.g., the joint) to which the external force is applied is determined using the joint torques. The system and method advantageously convert the joint torques to the external force that is compatible with the same admittance controller used with a force/torque sensor providing user input force into the system. Thus, the system and method integrate naturally with existing admittance control schemes. Furthermore, by accounting for the location of the applied external force in the virtual simulation, dynamic behavior of the robot becomes more predictable thereby increasing robustness and control of the robot. The user of the robotic system can control the manipulator by applying force to the surgical tool and by backdriving the manipulator by applying the external force to the manipulator. This may allow the user to grossly position the manipulator with ease. Alternatively, by accounting for the applied external force in the virtual simulation, the system and method can react to undesired collisions between the manipulator and objects in the vicinity of the manipulator. Moreover, by performing the described steps of the method for each joint individually, the resulting motion of the robot is natural and mimics the motion of an impedance control robot. As such, the system and method advantageously provide the benefits of impedance and admittance control systems.

BRIEF DESCRIPTION OF THE DRAWINGS

Advantages of the present invention will be readily appreciated as the same becomes better understood by reference to the following detailed description when considered in connection with the accompanying drawings.

DETAILED DESCRIPTION

I. Manipulator Overview

Referring to the Figures, wherein like numerals indicate like or corresponding parts throughout the several views, a robotic surgical system (hereinafter "system") 10 and method for operating the same are shown throughout.

Figure 1:
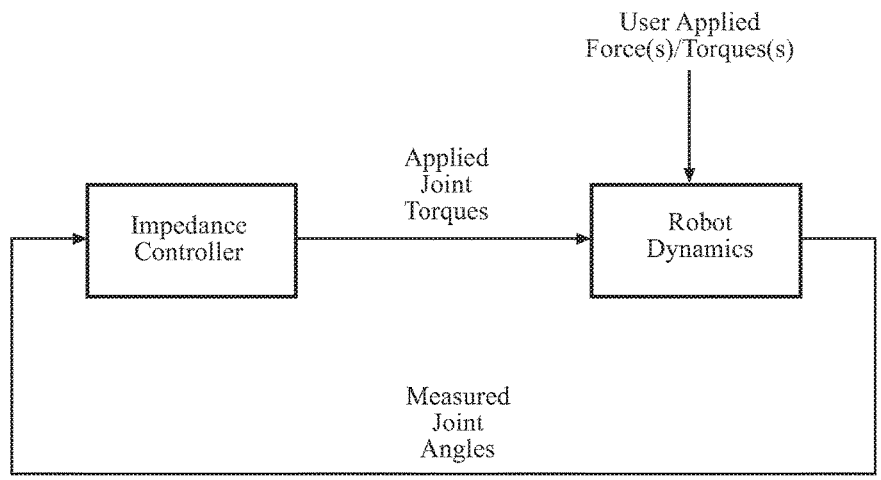
FIG. 1 is a flowchart of one example of a conventional impedance control loop.
Figure 2:
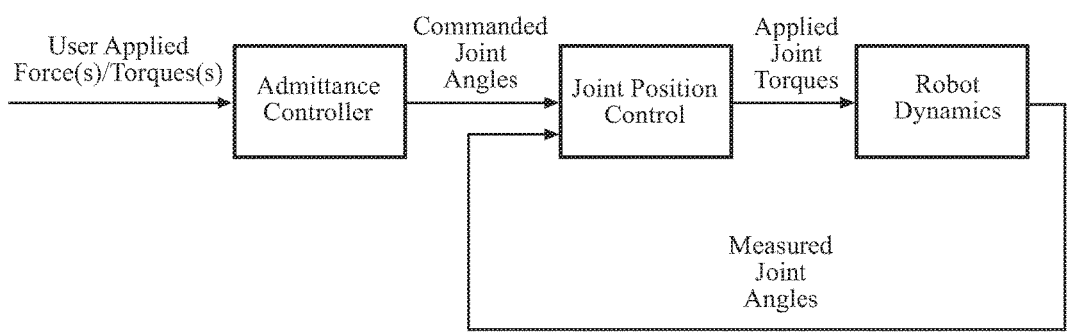
FIG. 2 is a flowchart of one example of a conventional admittance control loop.
Figure 3:
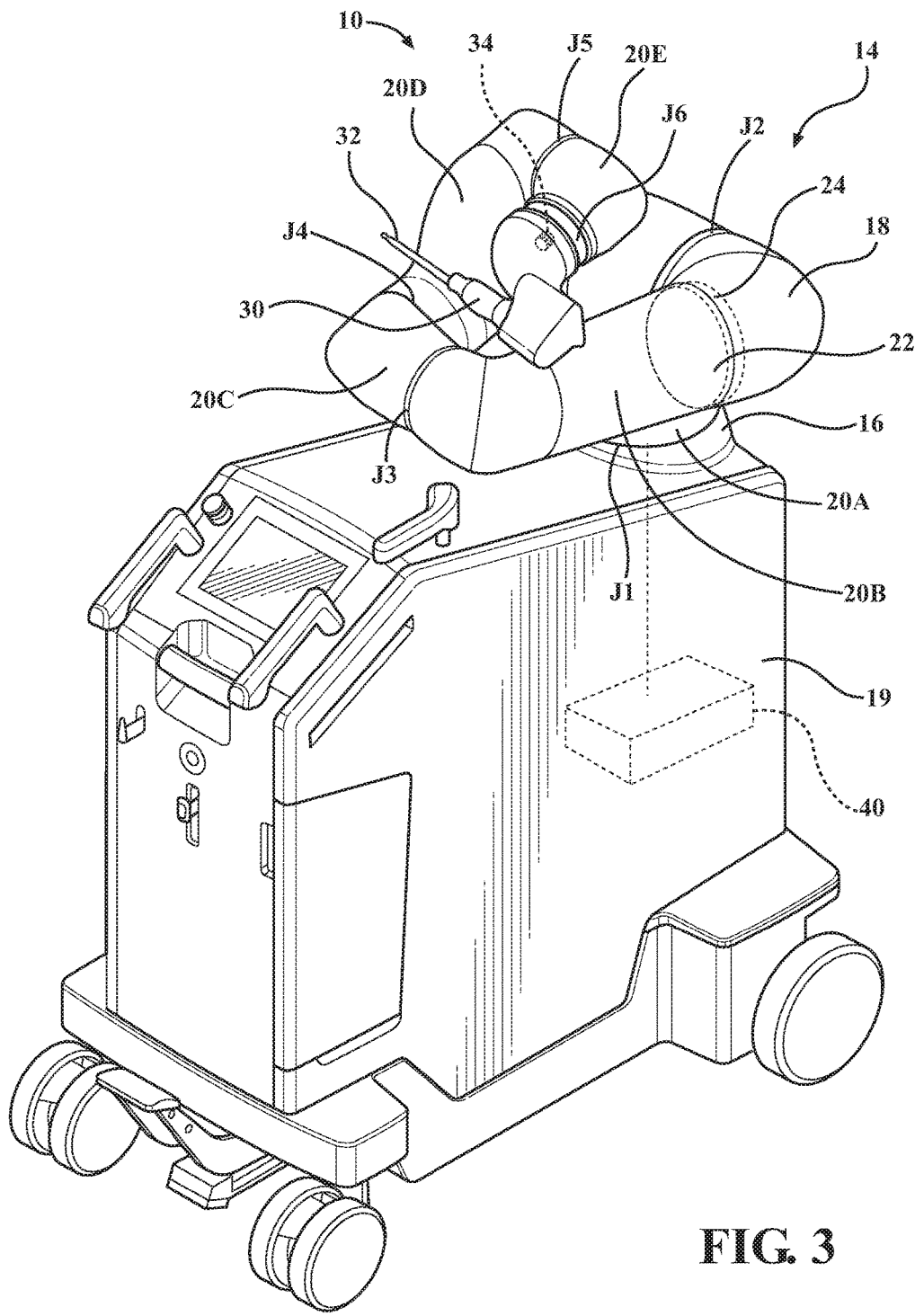
FIG. 3 is a perspective view of a robotic system including a manipulator, a controller, and a tool, according to one embodiment.

As shown in FIG. 3, the system 10 is a robotic surgical system for cutting away material from an anatomy of the patient, such as bone or soft tissue during a surgical procedure. The anatomy may be a femur, a tibia, a pelvis or any other anatomical part of the patient. The surgical procedure may involve partial or total knee or hip replacement surgery. The system 10 may also be designed to cut away material to be replaced by surgical implants such as hip and knee implants, including unicompartmental, bicompartmental, or total knee implants. The system 10 and method disclosed herein may alternatively be used to perform other procedures, surgical or non-surgical, or may be used in industrial applications or other applications where robotic systems are utilized.

As shown in FIG. 3, the system 10 includes a manipulator 14. The manipulator 14 has a base 16 and an arm (linkage) 18. The manipulator 14 may be coupled to a portable cart 19 for moving the manipulator 14 near the surgical site. The arm 18 may comprise a plurality of links 20 that are interconnected. These links 20 may be connected together in series and/or parallel. As such, the manipulator may have a serial arm or parallel arm configuration.

The manipulator 14 comprises a plurality of joints 22. Each pair of adjacent links 20 is connected by one of the joints 22. At each joint 22, there is an actuator, such as a joint motor 24 disposed between adjacent links 20. The joint motors 24 are configured to rotate the links 20. As such, positions of the links 20 are set by joint motors 24.

Each joint motor 24 may be attached to a structural frame internal to the manipulator. In one example, the joint motor 24 is a servo motor, such as a permanent magnet brushless motor. However, the joint motor 24 may have other configurations, such as synchronous motors, brush-type DC motors, stepper motors, induction motors, and the like.

Each joint 22 is actively driven by one of the joint motors 24. Utilization of the methods described herein may, at times, give the impression that some of the joints 22 are passive, meaning that the joint 22 is moved directly by the force exerted by the user (similar to a door joint). However, the joints 22 in the embodiments described herein are not passive. The system 10 and method mimic passive behavior by actively driving the joints 22 and thereby commanding control of the manipulator 14 in response to determined forces applied to the manipulator 14. This behavior is described in detail below.

The joint motors 24 are positioned at one of a plurality of angular positions, hereinafter referred to as joint angles. The joint angle is the angle of the joint 22 between adjacent links 20. Each joint motor 24 may be equipped with a position sensor 26. Alternatively, each link 20 being driven by that particular joint motor 24 may be equipped with the position sensor 26. One example of the position sensor 26 is an encoder that measures the joint angle of the respective joint 22. In some embodiments, two encoders, one for the joint motor 24 and one for the link 20 being moved can be used to determine the joint angle, such as by averaging the joint angle, and the displacement between motor and joint through the compliant transmission.

Each joint 22 is configured to undergo a joint torque. The joint torque is a turning or twisting "force" of the joint 22 and is a function of the force applied at a length from a pivot point of the joint 22. A torque sensor 28 may be connected to one or more joint motors 24 for measuring the joint torque of the joint 22. Alternatively, signals representative of currents applied to the joint motors 24 may be used to measure the joint torques.

As shown in FIG. 3, a tool 30, such as a surgical tool, couples to the manipulator 14 and is movable relative to the base 16 to interact with the surgical environment, and more specifically, the anatomy. The manipulator 14 supports the tool 30. The tool 30 is connected to the distal end of the arm 18. The manipulator 14 positions and orients the tool 30 so that the tool 30 performs the intended medical/surgical procedure on the patient. The tool 30 is grasped by an operator of the system 10. The tool 30 includes an energy applicator 32 designed to contact the tissue of the patient at the surgical site. The energy applicator 32 may be a drill, a burr, a sagittal saw blade, an ultrasonic vibrating tip, a probe, a stylus, or the like. The tool 30 and the manipulator 14 physically move with respect to a coordinate system. In one embodiment, the coordinate system is joint space comprising a vector including of all the joint angles of the manipulator 14. The manipulator 14 and the tool 30 may be arranged according to various configurations.

Figure 4:
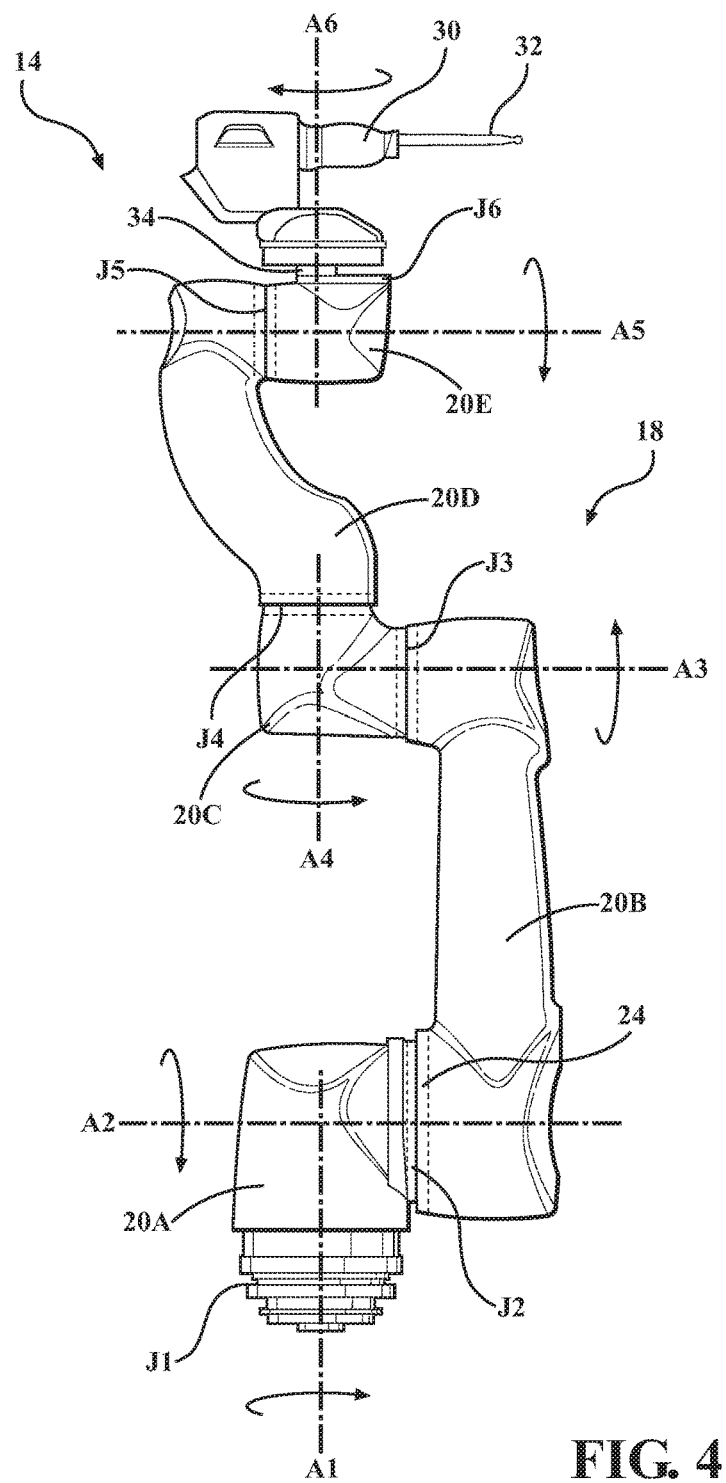
FIG. 4 is a front view of the manipulator of the robotic system according to one embodiment.

One example of the manipulator 14 is shown in FIG. 4. In this example, the manipulator 14 has a serial arm configuration. More specifically, the manipulator 14 includes five links 20a, 20b, 20c, 20d, 20e, wherein link 20a is most proximal to the base 16 and link 20e is most distal to the base 16. The manipulator 14 in FIG. 4 also comprises six joints 22, hereinafter identified as J1, J2, J3, J4, J5, J6. Joint J1 is disposed between the base 16 and link 20a. Joint J2 is disposed between link 20a and link 20b. Joint J3 is disposed between link 20b and link 20c. Joint J4 is disposed between link 20c and link 20d. Joint J5 is disposed between link 20d and link 20e. Joint J6 is disposed between link 20e and the tool 30. Since the manipulator 14 in FIG. 4 is a serial arm, movement of any one joint J1-J6 causes movement to all links downstream (i.e., all links from the moved joint to the distal end of the manipulator).

Each joint J1-J6 is configured to rotate about its own individual axis A1, A2, A3, A4, A5, A6, respectively. By having the six joints, J146, the manipulator 14 of FIG. 4 is free to move in 6DOF. That is, the manipulator 14, as a whole, is free to move forward/backward, up/down, and left/right translationally along in three perpendicular axes. The manipulator 14 is also free to change orientation through rotational movement about the three perpendicular axes, often termed pitch, yaw, and roll. Those skilled in the art appreciate that the manipulator 14 may only require movement in 5DOF depending on whether or not the tool 30 needs to be rotated about its own axis. For example, when burring, the manipulator 14 only needs to operate in 5DOF since the burr separately rotates. In such instances, there is redundancy because the number of joints is greater than the number of degrees-of-freedom required). However, when sawing, the manipulator 14 operates in 5DOF providing one degree of redundancy.

Joint J1, located at the base 16, effects movement similar to rotating of a waist. By rotating about axis A1, joint J1 allows the manipulator 14 to rotate from left to right. Joint J2 effects movement similar to rotating of a shoulder. By rotating about axis A2, joint J2 allows the manipulator 14 to extend forward and backward. Joint J3 effects movement similar to bending of an elbow. By rotating about axis A3, joint J3 allows the manipulator 14 to raise and lower. Joint J4 effects movement similar to twisting of a wrist. By rotating about axis A4, joint J4 allows the manipulator 14 to rotate the upper links 20d, 20e in a circular motion thereby changing orientation of the tool 30. Joint J5 effects movement similar to bending of a wrist. By rotating about axis A5, joint J5 allows the link 20e and the surgical tool 30 to tilt up and down and is responsible for pitch and yaw motion. Similar to J4, joint J6 effects movement similar to twisting of a wrist. However, joint J6 rotates about axis A6 to allow more precise control of the tool 30.

A sensor 34, such as a force-torque sensor, may be mounted between the distal link 20e and the tool 30. The force-torque sensor 34 is configured to output variable signals as a function of a force and/or a torque to which the tool 30 is exposed as the operator grasps the tool 30. By doing so, the force-torque sensor 34 allows sensing of an input force applied to the tool 30. As is described below, the input force is utilized to control movement of the manipulator 14. In one embodiment, the force-torque sensor 34 is a 6DOF sensor such that the force-torque sensor 34 is configured to outputs signals representative of three mutually orthogonal forces and three torques about the axes of the orthogonal forces that are applied to the tool 30. Additionally or alternatively, the input force applied to the tool 26 may be determined using joint torques, as is described in detail below.

II. Controller and Simulation Overview

Referring to FIG. 3, the system 10 includes a controller 40. The controller 40 is in communication with the manipulator 14 and includes suitable software and/or hardware for controlling the manipulator 14. In one embodiment, the controller 40 is disposed within the portable cart 19. However, the controller 40 includes sub-controllers disposed in more than one location. The controller 40 may control and be in communication with other systems not specifically described herein, such as navigation systems and the like.

Figure 5:
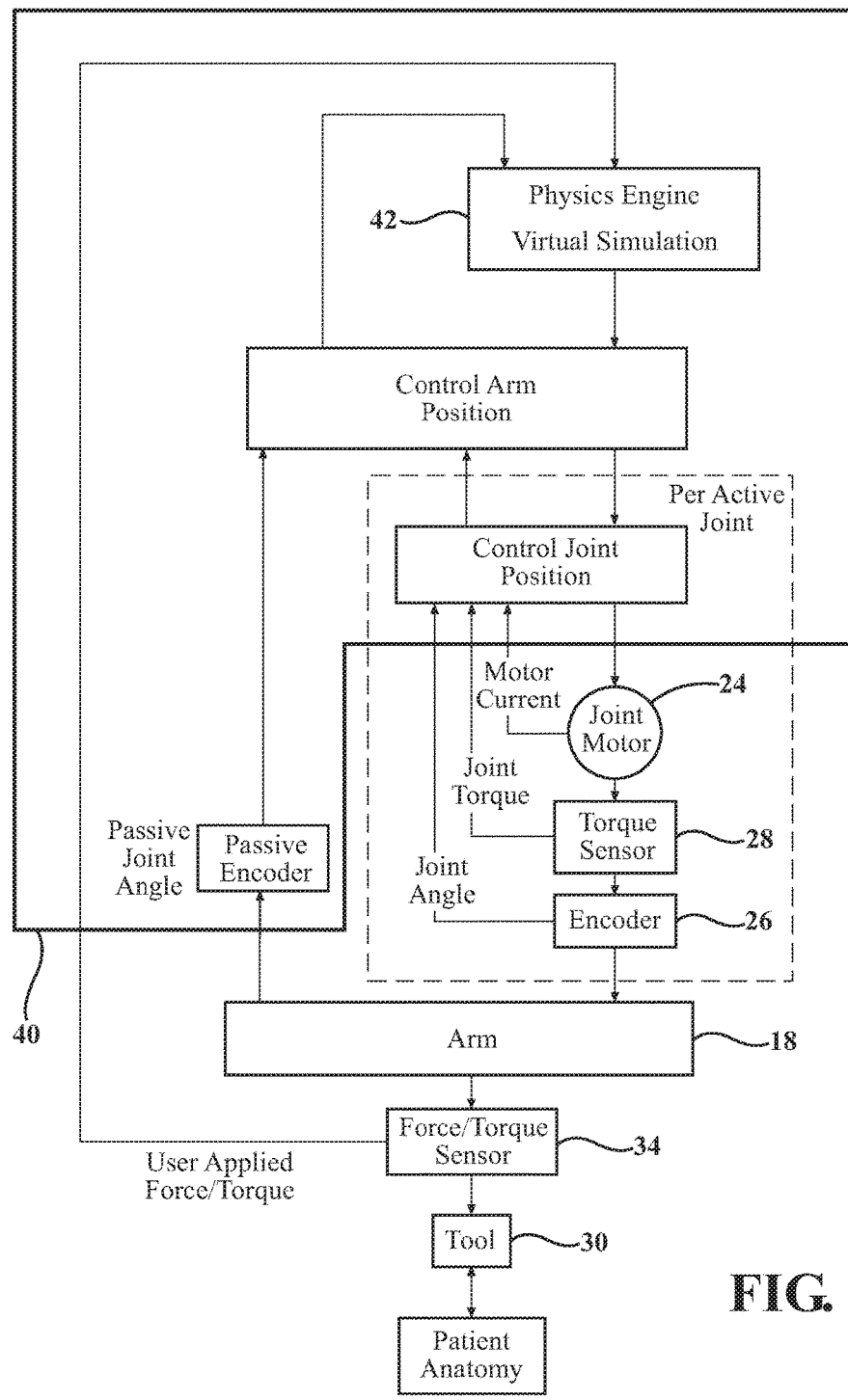
FIG. 5 is a block diagram of the robotic system illustrating interaction between the controller and the manipulator, according to one example.

As shown in FIG. 5, the controller 40 is in communication with the joint motors 24 for commanding movement and position of the links 20. The controller 40 is further connected to the position sensors (e.g., encoders) 26 and is configured to measure an actual joint angle of each respective joint 22 using signals received from the position sensors 26. The controller 40 commands the joint motors 24, such as through a joint motor subcontroller, to move to a commanded joint angle. The controller 40 is also connected to the torque sensor(s) 28 at the joint motors 24 for receiving signals indicative of the measured joint torque of the joint 22. The controller 40 further is connected to the force-torque sensor 34 for receiving the input force applied to the tool 30.

Figure 6:
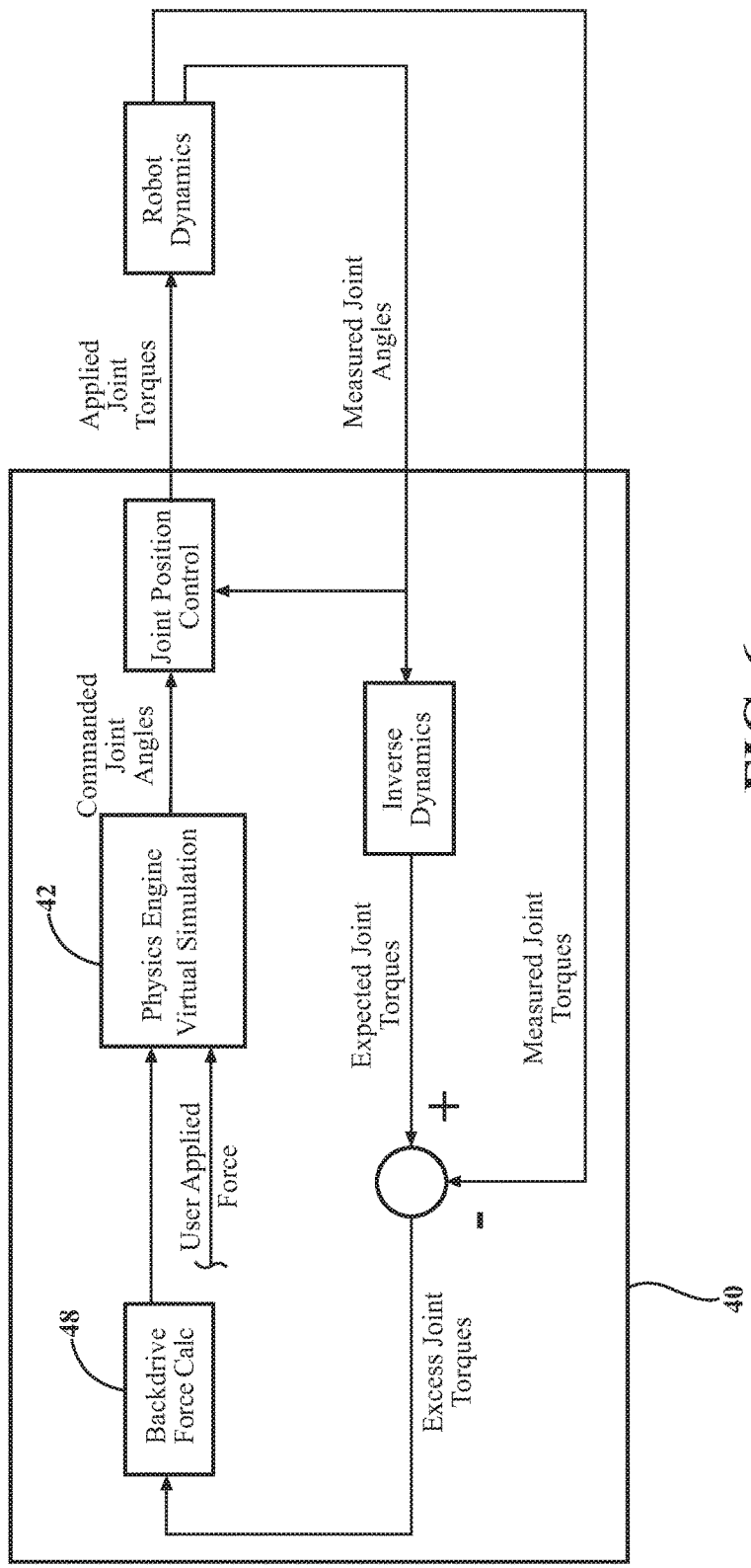
FIG. 6 is an exemplary flowchart of an improved admittance control loop according to the subject method.

As shown in FIG. 6, the controller 40 is an admittance-type controller. In other words, the controller 40 determines force and commands position. In one example, the controller 40 includes solely a single admittance controller such that all input forces are analyzed solely by the single controller 40 to determine the force. In other words, in this example, separate admittance controllers for different forces are not utilized. In other embodiments, additional controller may be used.

As shown in FIGS. 5 and 6, the controller 40 is configured to simulate dynamics of the tool 30 in a virtual simulation 42. The virtual simulation 42 may be based on the tool 30 with or without the energy applicator 32. In one embodiment, the virtual simulation 42 is implemented using a physics engine, which is computer software implemented by the controller 40 that simulates rigid body dynamics. The virtual simulation 42 may be implemented on a computing device having a non-transitory computer-readable storage medium with an executable program stored thereon. The virtual simulation 42 simulates dynamics of the tool 30 before such dynamics of the tool 30 are physically performed.

Figure 7:
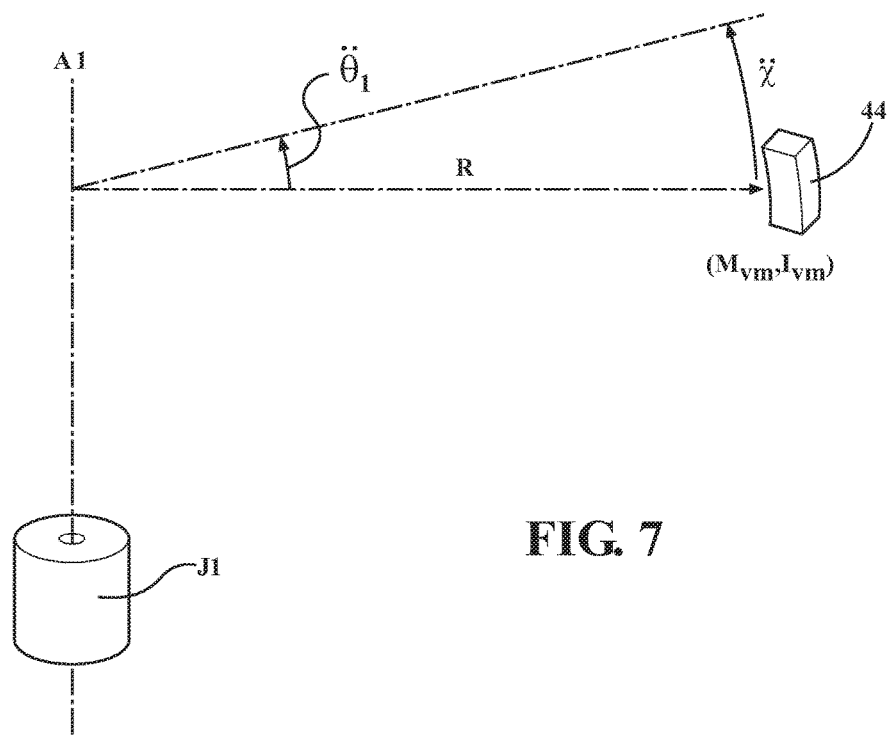
FIG. 7 is a conceptualization of calculations employed by the method wherein external force applied to a joint is calculated by projecting angular acceleration of the joint to a virtual mass corresponding to the tool to determine the acceleration of the virtual mass.

As shown in FIG. 7, the controller 40 models the tool 30 as a virtual rigid body 44 being a dynamic object. Therefore, the controller 40 effectively simulates rigid body dynamics of the tool 30. The virtual rigid body 44 is free to move according to 6DOF in Cartesian task space according to the virtual simulation 42. In FIG. 7, the virtual rigid body 44 may be modeled as a single point, which may be on, within, or beyond the tool 30. A mass/inertia matrix defines the virtual mass in 6DOF. As described below, the mass/inertia matrix is used in computational steps relating to backdriving.

In one example, the virtual rigid body 44 corresponds to a center of mass of the tool 30. Here "center of mass" is understood to be the point around which the tool 30 would rotate if a force is applied to another point of the tool 30 and the tool 30 were otherwise unconstrained, i.e., not constrained by the manipulator 14. The center of mass of the virtual rigid body 44 may be close to, but need not be the same as, the actual center of mass of the tool 30. The center of mass of the virtual rigid body 44 can be determined empirically. Once the tool 30 is attached to the manipulator 14, the position of the center of mass can be reset to accommodate the preferences of the individual practitioners. In other embodiments, the virtual rigid body 44 may correspond to other features of the tool 30, such as the center of gravity, or the like.

This virtual rigid body 44 is considered to have a virtual mass (M). The virtual mass has an inertia (I) about at least one of the joints 22. In some instances, the virtual mass has inertia about each one of the joints 22 (J1-J6). The inertia is a measure of a resistance that the virtual mass has to changes in velocity. The inertia may be understood to be a property of the virtual mass. As such, the virtual mass may refer to both the mass and inertia of the virtual rigid body 44. The virtual mass of the virtual rigid body 44 is typically within the same order of magnitude as an actual mass of tool 30. However, the virtual mass may be designed to be greater than or less than the actual mass of tool 30.

In one example, the virtual rigid body 44 is in a first pose at commencement of each iteration of the virtual simulation 42. The controller 40 receives the user applied input force from the force-torque sensor 34 and/or other input forces modeled as other constraints. The input forces are applied to the virtual rigid body 44 in the virtual simulation 42 when the virtual rigid body 44 is in the first pose. The input forces result in the virtual rigid body 44 advancing along a virtual path to a second pose having a different position and a different orientation within Cartesian space.

The virtual simulation 42 may be executed computationally without visual or graphical representations of the virtual rigid body 44. It is not necessary that the virtual simulation 42 virtually display dynamics the virtual rigid body 44 (such as is shown in FIG. 7). In other words, the virtual rigid body 44 need not be modeled within a graphics application executed on a processing unit. In some instances, movement of a virtual tool, which is tracked to the actual tool 30, may be displayed at the surgical site to provide visual assistance during operation of the procedure. However, in such instances, the displayed tool is not directly a result of the virtual simulation 42.

Knowing the second pose of the virtual rigid body 44 based on the virtual simulation 42, the controller 40 then commands action of the joints 22 in accordance with the virtual simulation 42. That is, the controller 40 converts the dynamics of the virtual rigid body 44 in Cartesian space to direct the motion of the manipulator 14 and control orientation of the tool 30 in joint space. The forces resulting in the second pose are applied to a Jacobian calculator, which calculates Jacobian matrices relating motion within Cartesian space to motion within joint space.

In one embodiment, and as shown in FIG. 6, the controller 40 is configured to determine the appropriate joint angles to command for the joints 22 based on the output of the virtual simulation 42. That is, the controller 40 computes the commanded joint angle for each of the joints 22 in response to the input force.

From here, the controller 40 regulates the joint angle of each joint 22 and continually adjusts the torque that each joint motor 24 outputs to, as closely as possible, ensure that the joint motor 24 drives the associated joint 22 to the commanded joint angle. In order to identify backdrive torques, the controller 40 determines an expected joint torque "$\tau_{expected}$" for each joint 22 using an inverse dynamics module. The expected joint torque is the torque that the joint motors 24 should output if external forces and torques are not present. Thus, the expected joint torque relates to the computed joint angle, joint velocity and joint acceleration for each of the joints 22.

The controller 40 is configured to apply signals to each joint motor 24 so that each joint motor 24 drives the associated joint 22 to the commanded joint angle. The controller 40 may use any suitable position control algorithms for controlling positioning the joints 22 based on the commanded joint angles. The controller 40 may generate the commanded joint angle only for those joints 22 that are active, i.e., expected to move based on the output of the virtual simulation 42.

In some embodiments, as represented in FIG. 5, the controller 40 generates the commanded joint angle for each of the joints 22 separately and individually (e.g., per each active joint). For example, the joints 22 may be considered in succession such that the commanded joint angle for J1 is generated first, and the commanded joint angle for J6 is generated last, or vice-versa.

As the joint motors 24 are energized to drive the joints to the commanded joint angles, the manipulator 14 undergoes dynamic movement, as represented by "robotic dynamic" block in FIG. 6. The controller 40 is configured to monitor commanded action of the at least one joint 22 and actual action of the at least one joint 22. More specifically, the controller 40 monitors the expected joint torque and compares it to an actual (measured) joint torque "$\tau_{actual}$" of the at least one joint 22.

Determining the actual joint torques may be implemented using the torque sensors 28 at the joint motors 24. Alternatively, the controller 40 is configured to measure electrical current drawn by the at least one joint motor 24 during positioning of the joint 22. Because torque is directly related to current draw, the controller 40 can analyze the measured current draw of the joint motor 24 to determine the actual joint torque of the joint 22. Any suitable sensing technology may be utilized to measure the current draw. For example, a current sensor may be disposed between a source of power and the joint motor 24. Feedback associated with the current sensing can be implemented directly by the controller 40 or separate from the controller 40. The controller 40 may take the force of gravity into effect when computing the current draw.

The expected joint torque may not correspond to the actual joint torque. Mainly, the joint 22 may experience external forces. Such external forces may be caused by the user applying force to one or more of the links 20. Alternatively, collision between the manipulator 14 and an object or obstacle may cause such external forces. Those skilled in the art appreciate that the other circumstances may cause such external forces. The external forces cause the actual joint torque to deviate from the expected joint torque. The ability of the manipulator 14 to respond to external forces applied to the arm 18 is herein referred to as "backdrivability." The manipulator 14 can be backdriven when external forces are applied to the arm 18 between the base 16 and the distal end of the arm. Thus, backdriving control is different than control based on the input force sensed by the force-torque sensor 34.

It should be clarified that although the external force, as described herein, may originate from environmental objects or conditions, e.g., operator interaction, collisions, and the like, the environmental object (e.g., operator) itself is not physically and directly moving the manipulator 14 to the intended positions. Instead, in many embodiments described herein, the external force is calculated and simulated to derive desired commands and movements to move the manipulator 14 thereby giving the appearance as though the environmental object itself is physically and directly moving the manipulator 14, when in fact it is not. Thus, with the system 10 and method, it can be said that all movements of the manipulator 14 are desired because all movements of the manipulator 14 are calculated.

As shown in FIG. 6, the controller 40 compares the expected joint torque to the actual joint torque of the at least one joint 22 to determine a joint torque difference $\Delta \tau$. In one embodiment, the joint torque difference for any given joint "i" is calculated as follows:

$$\Delta \tau_i = \tau_{expected} - \tau_{actual} \quad [1]$$

The joint torque difference may be understood to be an excess joint torque. In some embodiments, the controller 40 compares the expected joint torque to the actual joint torque for each of the joints 22 separately and individually. As described above, for example, the commanded and actual joint torques may be compared for each joint 22, in succession, and one at a time. The joint torque difference may exist for one joint 22 or for a plurality of joints 22. As such, this step may be performed in 1DOF.

Knowing the joint torque difference, the controller 40 is configured to determine an external force applied to at least one of the joints 22. The controller 40 converts the joint torque difference for each joint 22 (if present) into a 6DOF force/torque vector applied to the virtual mass. In other words, the external force causing the joint torque difference is converted into Cartesian space and accounted for in the virtual simulation 42. The dynamics of the virtual rigid body 44 are simulated to react based on the external force.

The controller 40 is configured to re-simulate dynamics of the tool 30 in the virtual simulation, as described above, by further taking into account the determined external force in addition to the input force. In other words, the excess joint torques are converted into a force compatible with an admittance controller utilizing the force-torque sensor 34. Similarly, the controller 40 is configured to re-command action of the joints 22 to the desired pose in accordance with the virtual simulation 42 accounting for both the input force and the external force.

As described, the controller 40 is configured to determine the external force applied to at least one of the joints 22 directly from the joint torque differences. The techniques described above account for the external force, but may result in unexpected joint movement. Mainly, determining the external force directly from the joint torque differences does not fully capture the location of the applied external force relative to the manipulator 14 because the external force is not decomposed in joint space. In other words, the controller 40 is not aware of where the external force is being applied on the manipulator 14.

Figure 8:
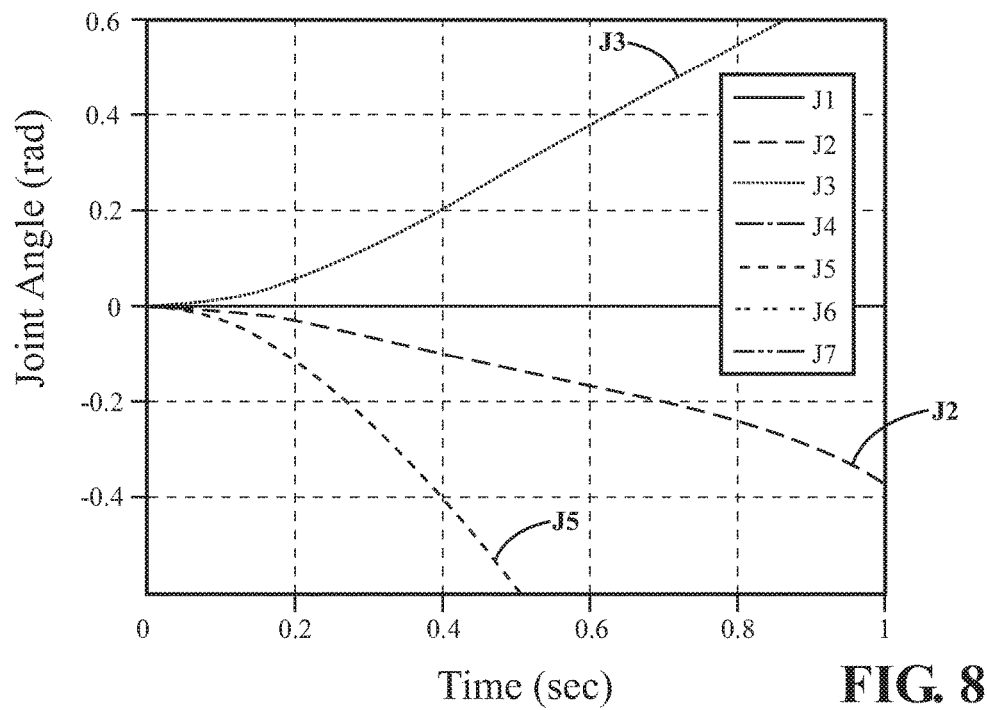
FIG. 8 is a chart illustrating joint movement in response to one example of an external force according to prior techniques.
Figure 9:
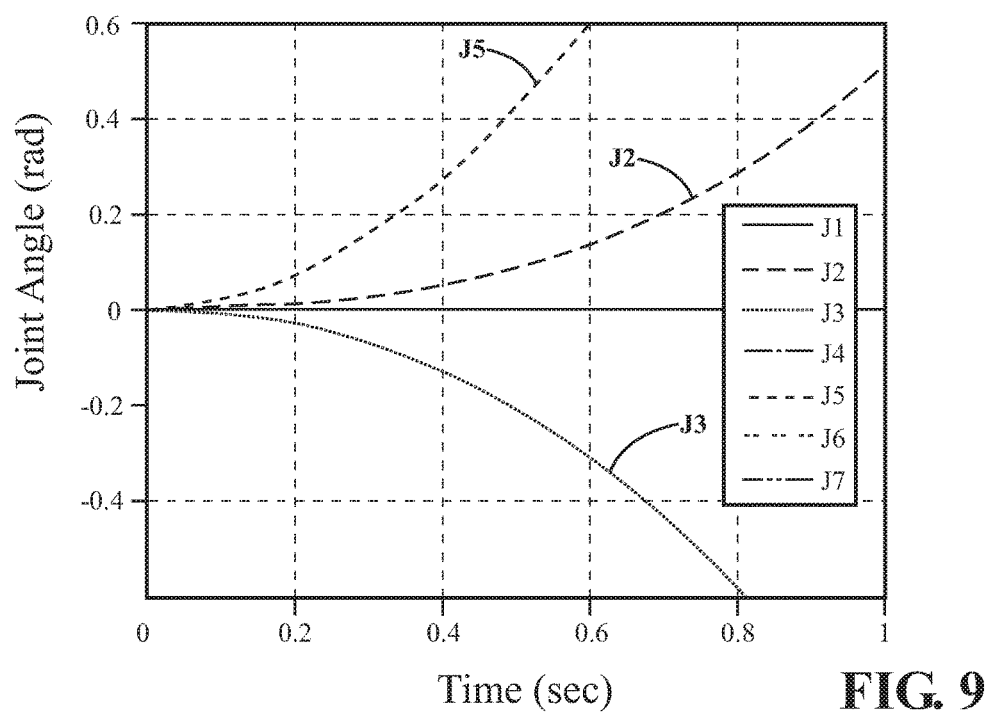
FIG. 9 is a chart illustrating joint movement in response to another example of external force according to prior techniques.

FIGS. 8 and 9 are graphs illustrating joint movement where external force is directly determined based on joint torque difference alone. In FIG. 8, the joint torque difference of −1.5 Nm is applied to J2. However, in response, J3 and J5 move unexpectedly. Thus, two other joints (i.e., J3 and J5) move although J2 is the only joint experiencing the change in torque from the external force. Similarly, in FIG. 9, the joint torque difference of −0.5 Nm is applied to J2 and J3. In response, J2 moves in the wrong direction and J5 moves unexpectedly. In other words, another joint (i.e., J5) moves although J2 and J3 are the only joints experiencing the change in torque from the external force. Furthermore, one of the joints (J2) experiencing the change in torque from the external force responds opposite to the external force.

III. Backdriving Method Overview

The robotic system 10 and method described in this section improve on the techniques described above by providing backdriving techniques resulting in predictable joint movement by decomposing the applied external force in joint space to fully capture the location of the external force relative to the manipulator 14. The system 10 and method implement this improved backdriving method at block 48 in FIG. 6. In essence, the method described below provides an enhancement relating to how the external force is calculated.

Figure 10:
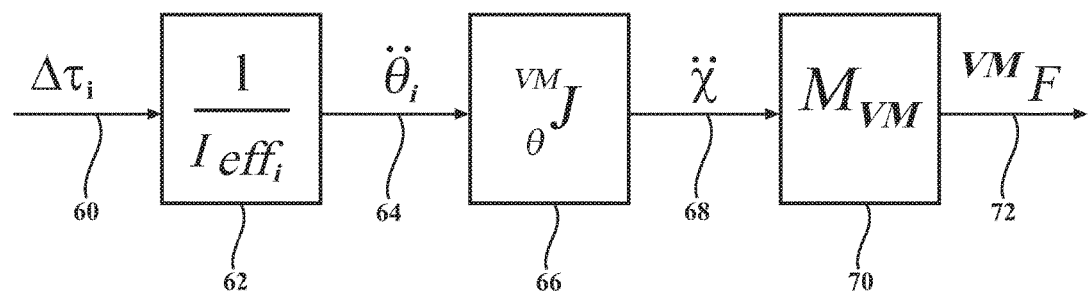
FIG. 10 is a simplified flowchart of the calculations performed by the method.

FIG. 10 illustrates a computational flowchart showing inputs and outputs of the backdriving method described below. As shown at step 60, the joint torque difference $\Delta \tau_i$ is computed for each individual joint "i" separately, as described above. As such, the joint torque differences are computed in 1DOF.

Next, at block 62, the controller 40 determines the inertia of the virtual mass about the at least one joint 22, and more specifically about the axis of the at least one joint 22. In one embodiment, the controller 40 determines the inertia of the virtual mass for each one of the joints 22 separately and individually. As such, the inertia of each joint may be computed in 1DOF. To conceptualize this step, FIG. 7 illustrates the relationship between the inertia of the virtual mass for one joint, i.e., J1, which is considered separately. However, the inertia of the virtual mass about any given joint is expressed as follows:

$$I_i = I_{vm} + m_{vm} R^2 \quad [2]$$

In equation [2], I is the inertia of the virtual mass about joint i, $m_{vm}$, $I_{vm}$ are the mass and inertia of the virtual rigid body 44 about the axis of the joint i as defined by the mass/inertia matrix, and R is the radius between the axis A of the joint and the virtual mass.

The inertia of the virtual mass about each joint can alternatively be expressed as an effective inertia of the virtual mass about joint axis i, generally as follows:

$$I_i = J^T M_{vm} J \quad [3]$$

and more specifically, as follows:

$$I_{\textit{eff}_i} = {}_{\theta_i}{}^{vm}J^T M_{vm\theta_i}{}^{vm}J \quad [4]$$

In equation [4], ${}_{\theta_i}{}^{vm}J^T$ is the Jacobian transpose mapping changes in virtual mass motion to changes in joint angles, $M_{vm}$ is the mass of the virtual rigid body 44 as defined by the mass/inertia matrix, and ${}_{\theta_i}{}^{vm}J$ is the Jacobian mapping changes in joint angles to changes in virtual mass motion. In equations [3] and [4], M is capitalized indicating that it is a matrix and not a scalar (as in equation [2]). Equations [3] and [4] are used to compute the 1DOF inertia $I_{\textit{eff}}$ from the 6DOF J and 6DOF $M_{vm}$. Using the Jacobian and 6DOF Mvm is more convenient than computing the 1DOF/vm about an arbitrary axis in equation [2], which can be difficult.

At step 64, the controller 40 is configured to compute an angular acceleration $\ddot{\theta}$ about the at least one joint 22 using the joint torque difference and the inertia. The angular acceleration $\theta_1$ about the axis A1 of J1 is illustrated in FIG. 7. In one embodiment, the controller 40 computes the angular acceleration $\ddot{\theta}_i$ about each joint i in 1DOF. In other words, using the excess torque, the controller 40 determines how the joint angle accelerates. The joint torque difference $\Delta \tau_i$ and the inertia $I_i$ for given joint i are inputted into the following equation such that the angular acceleration $\ddot{\theta}$ can be computed as follows:

$$\Delta \tau_i = I_i \ddot{\theta}_i \quad [5]$$

At step 66, the controller 40 is configured to project the angular accelerations relating to each joint 22 to the virtual mass. Unlike the previous steps, which perform the computational steps in 1DOF, the controller 40 preferably projects the angular acceleration to the virtual mass using the joints 22 in combination. Mainly, the controller combines the angular accelerations of the plurality of joints 22 in multi-DOF or 6DOF.

By projecting the angular accelerations, the controller 40 obtains an acceleration $\ddot{x}$ of the virtual mass in multi-DOF or 6DOF, at step 68. FIG. 7 conceptually illustrates the acceleration $\ddot{x}$ of the virtual mass according to one embodiment. The controller 40 obtains the acceleration of the virtual mass by projecting joint angle information from joint space to virtual mass motion in Cartesian space. More specifically, the acceleration of the virtual mass in multi-DOF or 6DOF is derived from the angular acceleration computed for each joint axis in 1DOF.

In one example, the acceleration of the virtual mass is computed as follows, wherein $\ddot{x}$ is the acceleration of the virtual mass, ${}_{\theta_i}{}^{vm}J$ is the Jacobian mapping changes in joint angles to changes in virtual mass motion, and $\ddot{\theta}_i$ is angular acceleration about each joint i:

$$\ddot{x} = {}_{\theta_i}{}^{vm}J \ddot{\theta}_i \quad [6]$$

Understood a different way, the controller compares a commanded joint angle to an actual joint angle for each of the joints 22 to determine a joint angle difference for each of the joints 22 in 1DOF. The controller 40 further compares a first motion of the virtual mass to a second motion of the virtual mass for each of the joints 22 to determine a motion difference for each of the joints 22 in 1DOF. The controller 40 then maps, in a Jacobian matrix, the joint angle difference for each of the joints and the motion difference for each of the joints in multi-DOF or 6DOF to obtain the acceleration $\ddot{x}$ of the virtual mass in multi-DOF or 6DOF.

At step 70, the controller 40 inputs the acceleration $\ddot{x}$ of the virtual mass in multi-DOF or 6DOF into the mass/inertia matrix defining the virtual mass in multi-DOF or 6DOF. The mass/inertia matrix is used to determine the force/torque to apply to the virtual mass in multi-DOF or 6DOF to produce the external force corresponding to the computed acceleration $\ddot{x}$. The 6DOF force/torque vector is computed by multiplying the 6DOF mass matrix Mvm and the 6DOF acceleration vector such that $F_{VM} = M_{vm} \ddot{x}$, where $F_{VM}$ is the same as $V_{MF}$.

At step 72, the external force $VM_F$ is computed as an output of inputting the acceleration $\ddot{x}$ of the virtual mass in multi-DOF or 6DOF into the mass/inertia matrix. As described above, the controller 40 thereafter simulates dynamics of the tool 30 in the virtual simulation 42 in response to the external force and the input force(s), if present, from the force-torque sensor or joints 22. The controller 40 re-commands action of the joints 22 to the desired pose in accordance with the virtual simulation 42 accounting for the external force and input force(s), if present.

In one embodiment, a force summer sums the external force and the input force(s) and the controller 40 can then compute a commanded position of the tool 30 based on the summed total force $F_{total}$ by solving for $F_{total} = M_{vm} \ddot{x}_t$ to find $\ddot{x}_t$. After the acceleration $\ddot{x}_t$ is solved for, $\ddot{x}_t$ can be integrated twice to compute a commanded next position. The commanded position in Cartesian space is converted to commanded joint angles in joint space.

The system 10 and method may utilize the backdriving technique described herein for several different applications or situations. In one example, the user of the robotic system 10 can control the manipulator 14 by applying force to the surgical tool 30 and by backdriving the manipulator 14 by applying the external force to any given joint(s) 22 or link(s) 22. This may allow the user to grossly position the manipulator 14 with ease. Such application may be particularly useful when setting up the manipulator 14 at the work site. In other instances, the user may apply the external force while controlling the manipulator 14 during fine positioning in order to reposition one or more links 22 for comfort or space considerations. In either instance, the controller 40 takes into account the applied external force when commanding the manipulator 14 such that full backdriving control of the manipulator is possible.

Alternatively, by accounting for the applied external force in the virtual simulation, the system 10 and method can react to undesired collisions between the manipulator 14 and objects in the vicinity of the manipulator 14 or objects interfering with the path of movement of the manipulator 14. In such instances, it may be undesired to allow the manipulator 14 to react to the external force. Thus, in such instances, the controller 40 takes into account the applied external force, but may negate the external force, or completely halt the manipulator 14 as a precaution.

In other examples, the backdriving technique may be utilized during a manual mode of operation. During the manual mode, the operator manually directs, and the manipulator 14 controls, movement of the tool 30. The operator physically contacts the tool 30 to cause movement of the tool 30. The manipulator 14 monitors the forces and torques placed on the tool 30 using the force-torque sensor 34. The operator may backdrive any given joint while the controller 40 controls the manipulator 14 in response to the forces and torques detected by the force-torque sensor 34.

In another application, the manipulator 14 directs autonomous movement of the tool 30 in an autonomous mode of operation. Here, the manipulator 14 is capable of moving the tool 30 free of operator assistance. Free of operator assistance may mean that an operator does not physically contact the tool 30 to apply force to move the tool 30. Instead, the operator may use some form of control to remotely manage starting and stopping of movement. For example, the operator may hold down a button of a remote control to start movement of the tool 30 and release the button to stop movement of the tool 30.

In one instance, the positioning of the tool 30 may be maintained at the worksite during autonomous mode. However, the operator may desire to re-orient the tool 30. Reorientation of the tool 30, while maintaining position, may further require the downstream links 20 to be re-oriented. The backdriving techniques described herein may be utilized to account for external force applied to the links 20 to re-orient the tool 30 in autonomous mode. Those skilled in the art will appreciate that various other applications or situations may utilize the backdriving techniques described herein.

The backdriving techniques described in this section take into account the location of the external force relative to the manipulator 14. By decomposing the external force in joint space to each individual joint, the method accounts for the location of the applied external force in the virtual simulation 42. This way, when the controller 40 commands the manipulator 14 by accounting for the external force, the joints 22 of the manipulator 14 exhibit predictable movement. Dynamic behavior of the manipulator 14 becomes more predictable thereby increasing robustness and control of the manipulator 14. Using the aforementioned technique, the system 10 and method advantageously convert the joint torques to the external force that is compatible with the same admittance controller 40 used with the force/torque sensor 34 providing input force. Meanwhile, by performing the described steps of the method for each joint 22 individually, the resulting motion of the manipulator 14 is natural and mimics the motion of an impedance control robot.

Figure 11:
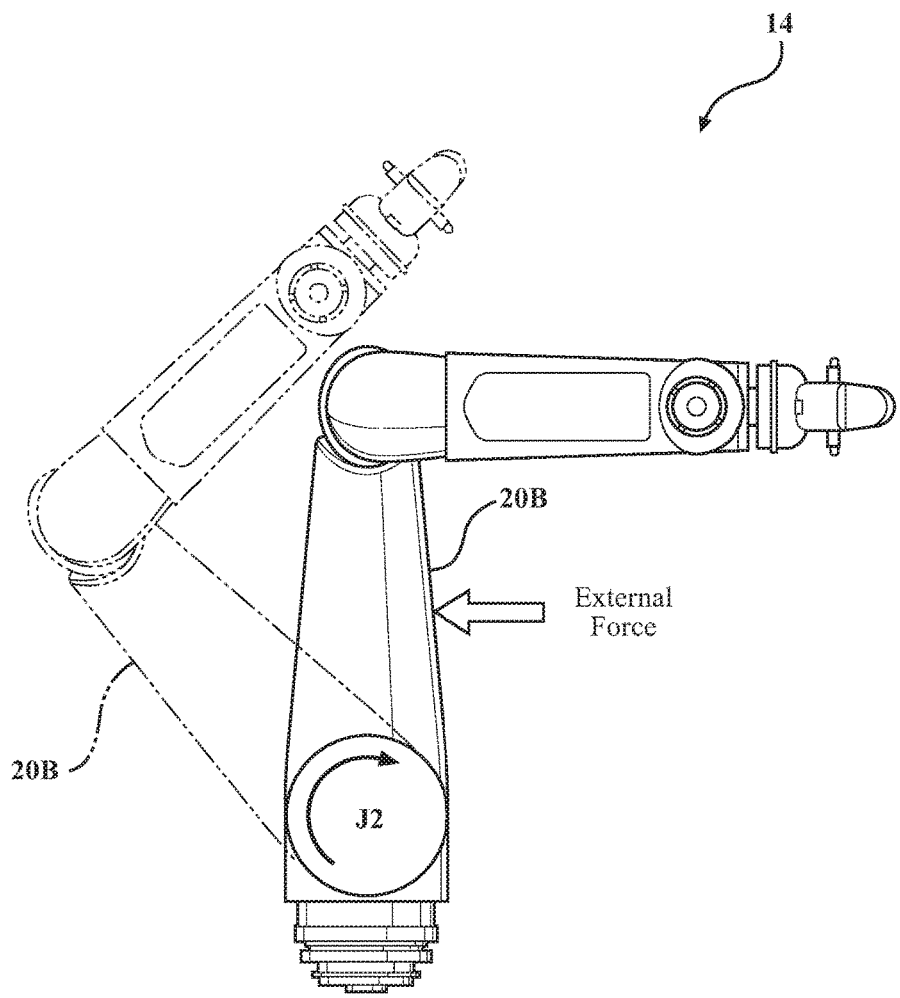
FIG. 11 is a side view of the manipulator of FIG. 4 illustrating an example of movement of the manipulator between two poses according to the backdriving techniques of the subject method.
Figure 12:
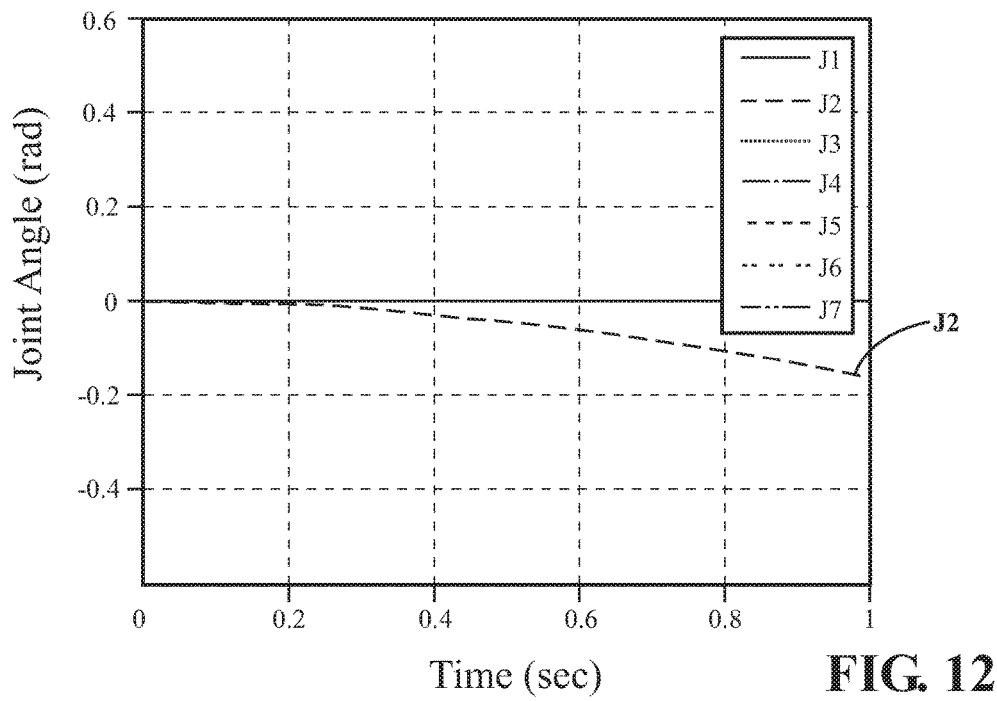
FIG. 12 is a chart illustrating joint movement according to the subject method in response to the same example of the external force applied in FIG. 8.

To conceptualize this improved behavior, FIG. 11 illustrates a side view of the manipulator 14 in the first pose (shown in solid lines). The external force is applied to joint J2. The system 10 and method perform the aforementioned steps to effectively compensate for the external force in the virtual simulation 42. The controller 40 commands action of the joint J2 to the desired second pose (shown in phantom lines). FIG. 12, relating to movement of the manipulator 14 in FIG. 11, is a graph illustrating joint movement where external force is determined using the steps described in this section (as compared with FIG. 8 illustrating joint movement where external force is determined based on joint torque difference alone). In FIG. 11, the joint torque difference of −1.5 Nm is applied to J2. For comparative purposes, this is the same joint torque difference applied to J2 in FIG. 8. In response, only joint J2 moves (as also shown in FIG. 11). Unlike the joints in FIG. 8, no other joints move unexpectedly. In other words, other joints (e.g., J3 and J5) do not move because J2 is the only joint experiencing the change in torque from the external force. Referring back to FIG. 11, movement of the manipulator 14 is consistent with the results of FIG. 12 wherein only joint J2 moves in response to the external force.

Figure 14:
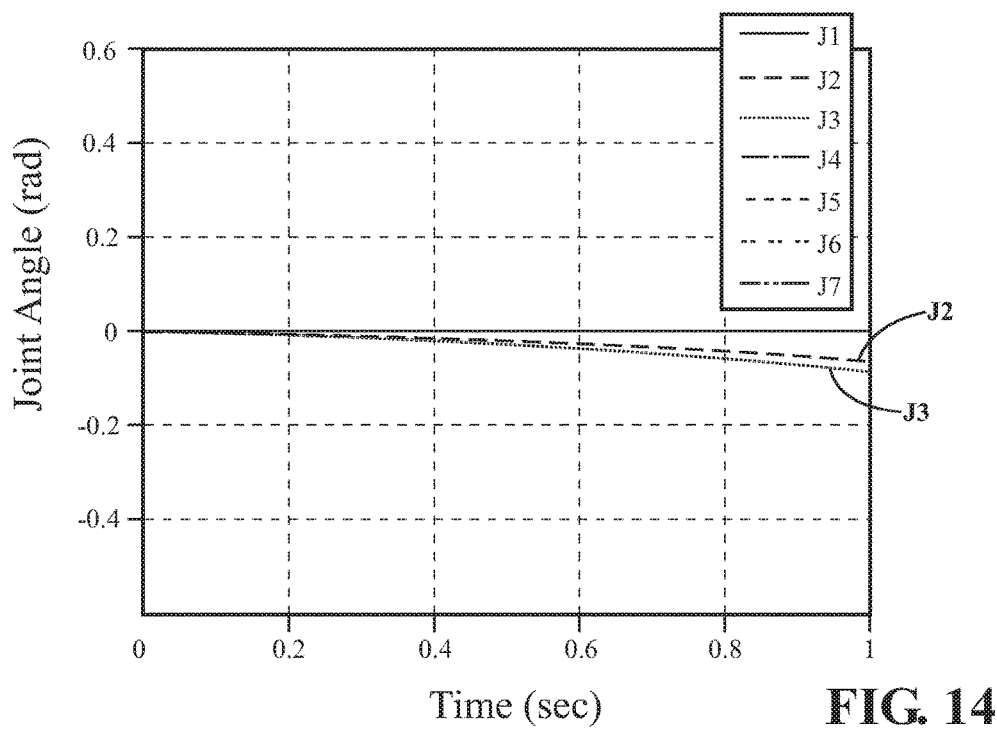
FIG. 14 is a chart illustrating joint movement according to the subject method in response to the same example of the external force applied in FIG. 9.
Figure 13:
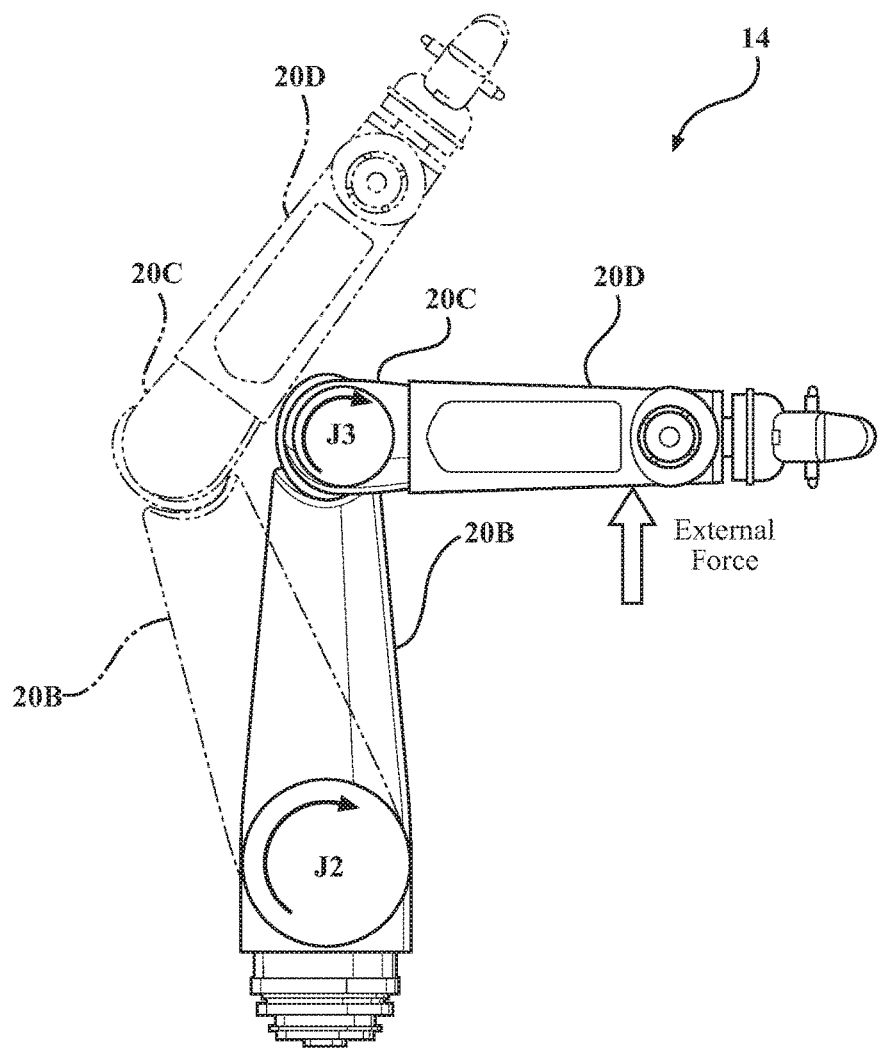
FIG. 13 is a side view of the manipulator of FIG. 4 illustrating another example of movement of the manipulator between two poses according to the backdriving techniques of the subject method.

FIG. 13 illustrates a side view of the manipulator 14 in the first pose using solid lines. In this example, the external force is applied to joints J2 and J3. The system 10 and method perform the aforementioned steps to effectively compensate for the external force in the virtual simulation 42. The controller 40 commands action of the joint J2 and J3 to the desired second pose (shown in phantom lines) in the direction of the applied torque. FIG. 14, corresponding to movement of the manipulator 14 in FIG. 13, is a graph illustrating joint movement where external force is determined using the steps described in this section (as compared with FIG. 9 illustrating joint movement where external force is determined based on joint torque difference alone). In FIG. 13, the joint torque difference of −0.5 Nm is applied to J2 and J3. For comparative purposes, this is the same joint torque difference applied to J2 and J3 in FIG. 9. In response, only joint J2 and J3 move. Unlike the joints in FIG. 9, no other joints move unexpectedly and no joints move in the wrong direction. In other words, other joints (e.g., J5) do not move because J2 and J3 are the only joints experiencing the change in torque from the external force. Additionally, J2 and J3 move in the direction of the applied torque (and not in other directions). Referring back to FIG. 13, movement of the manipulator 14 is consistent with the results of FIG. 13 wherein only joints J2 and J3 move in response to the external force.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A robotic surgical system comprising:
   a surgical tool;
   a manipulator supporting said surgical tool and comprising a plurality of joints and a plurality of joint actuators; and
   a controller being in communication with said manipulator and being configured to simulate dynamics of said surgical tool in a virtual simulation by representing said surgical tool as a virtual rigid body having a virtual mass with said virtual mass having an inertia about at least one of said joints;
   said controller being configured to:
   determine an expected joint torque for said at least one joint,
   compare said expected joint torque to an actual joint torque of said at least one joint to determine a joint torque difference,
   determine said inertia of said virtual mass about said at least one joint,
   compute an angular acceleration about said at least one joint using said joint torque difference and said inertia,
   project said angular acceleration to said virtual mass to determine an external force by combining said angular accelerations of said plurality of joints to obtain an acceleration of said virtual mass in six-degrees of freedom (6DOF), simulate dynamics of said surgical tool in said virtual simulation in response to said external force, and command action of said joint actuators in accordance with said virtual simulation.

2. The robotic surgical system of claim 1 wherein said controller is further configured to: determine said expected joint torque, compare said expected joint torque to said actual joint torque, determine said inertia of said virtual mass, and compute said angular acceleration, for each one of said joints individually.

3. The robotic surgical system of claim 1 wherein said controller is further configured to simulate dynamics of said surgical tool, by using said plurality of joints in combination.

4. The robotic surgical system of claim 1 wherein said controller is further configured to obtain said acceleration of said virtual mass by comparing a commanded joint angle to an actual joint angle for each of said joints to determine a joint angle difference for each of said joints.

5. The robotic surgical system of claim 4 wherein said controller is further configured to obtain said acceleration of said virtual mass by comparing a first motion of said virtual mass to a second motion of said virtual mass for each of said joints to determine a motion difference for each of said joints.

6. The robotic surgical system of claim 5 wherein said controller is further configured to obtain said acceleration of said virtual mass by mapping in a Jacobian matrix said joint angle difference for each of said joints and said motion difference for each of said joints.

7. The robotic surgical system of claim 1 wherein said controller is further configured to project said angular acceleration to said virtual mass to determine said external force by inputting said acceleration of said virtual mass in 6DOF into a mass/inertia matrix defining said virtual mass in 6DOF to determine said external force.

8. The robotic surgical system of claim 1 further comprising a force-torque sensor for sensing an input force applied to said surgical tool.

9. The robotic surgical system of claim 8 wherein said controller is further configured to re-simulate dynamics of said surgical tool in said virtual simulation in response to both said input force and said external force and re-command action of said joint actuators in accordance with said virtual simulation taking into account both said input force and said external force.

10. A method of operating a robotic surgical system comprising a surgical tool, a manipulator supporting the surgical tool and comprising a plurality of joints, and a plurality of joint actuators, and a controller being in communication with the manipulator, and a virtual simulation representing the surgical tool as a virtual rigid body having a virtual mass with the virtual mass having an inertia about at least one of the joints, the method comprising the controller:

determining an expected joint torque for the at least one joint;

comparing the expected joint torque to an actual joint torque of the at least one joint to determine a joint torque difference;

determining the inertia of the virtual mass about the at least one joint;

computing an angular acceleration about the at least one joint using the joint torque difference and the inertia;

projecting the angular acceleration to the virtual mass to determine an external force by combining the angular accelerations of the plurality of joints to obtain an acceleration of the virtual mass in six-degrees of freedom (6DOF);

simulating dynamics of the surgical tool the virtual simulation in response to the external force; and commanding action of the joint actuators in accordance with the virtual simulation.

11. The method of claim 10 wherein the steps of determining the expected joint torque, comparing the expected joint torque to the actual joint torque, determining the inertia of the virtual mass, and computing the angular acceleration, are each performed for each one of the joints individually.

12. The method of claim 10 wherein the step of simulating dynamics of the surgical tool is performed by using the plurality of joints in combination.

13. The method of claim 10 wherein the step of obtaining the acceleration of the virtual mass further comprises comparing a commanded joint angle to an actual joint angle for each of the joints to determine a joint angle difference for each of the joints.

14. The method of claim 13 wherein the step of obtaining the acceleration of the virtual mass further comprises comparing a first motion of the virtual mass to a second motion of the virtual mass for each of the joints to determine a motion difference for each of the joints.

15. The method of claim 14 wherein the step of obtaining the acceleration of the virtual mass further comprises mapping in a Jacobian matrix the joint angle difference for each of the joints and the motion difference for each of the joints.

16. The method of claim 10 wherein the step of projecting the angular acceleration to the virtual mass to determine the external force further comprises inputting the acceleration of the virtual mass in 6DOF into a mass/inertia matrix defining the virtual mass in 6DOF to determine the external force.

17. The method of claim 10 further comprising the step of sensing an input force applied to the surgical tool from a force-torque sensor.

18. The method of claim 17 further comprising the step of re-simulating with the controller dynamics of the surgical tool in the virtual simulation in response to both the input force and the external force and the step of re-commanding action of the joint actuators in accordance with the virtual simulation taking into account both the input force and the external force.

19. A method of backdriving a robotic system comprising a tool, a manipulator supporting the tool and comprising a plurality of joints, a plurality of joint actuators, and a controller being in communication with the manipulator, and a virtual simulation representing the tool as a virtual rigid body having a virtual mass with the virtual mass having an inertia about each of the joints, the method comprising the controller:

determining an expected joint torque for each joint individually;

comparing the expected joint torque to an actual joint torque to determine a joint torque difference for each joint individually;

determining the inertia of the virtual mass about each joint individually;

computing an angular acceleration about each joint individually using the joint torque difference and the inertia;

obtaining an acceleration of the virtual mass in more than one degree of freedom using the angular accelerations of the plurality of joints in combination;

projecting the angular acceleration to the virtual mass in more than one degree of freedom to determine an external force;

simulating dynamics of the tool in the virtual simulation in response to the external force; and commanding action of the joint actuators in accordance with the virtual simulation.

20. The method of claim 19, wherein obtaining an acceleration of the virtual mass in more than one degree of freedom using the angular accelerations of the plurality of joints in combination further comprises:

comparing a commanded joint angle to an actual joint angle for each of the joints to determine a joint angle difference for each of the joints;

comparing a first motion of the virtual mass to a second motion of the virtual mass for each of the joints to determine a motion difference for each of the joints; and mapping in a Jacobian matrix the joint angle difference for each of the joints and the motion difference for each of the joints.

21. The method of claim 19 wherein the step of projecting the angular acceleration to the virtual mass in more than one degree of freedom to determine the external force further comprises inputting the acceleration of the virtual mass in 6DOF into a mass/inertia matrix defining the virtual mass in 6DOF to determine the external force.

* * * * *